US010955386B2

United States Patent
Doyle et al.

(10) Patent No.: US 10,955,386 B2
(45) Date of Patent: Mar. 23, 2021

(54) COMPACT IMMERSION SCANNING SYSTEM FOR HIGH-FREQUENCY SOUND WAVES

(71) Applicant: Utah Valley University, Orem, UT (US)

(72) Inventors: Timothy E. Doyle, Orem, UT (US); Huda A. Al-Ghaib, Vineyard, UT (US)

(73) Assignee: Utah Valley University, Orem, UT (US)

( * ) Notice: Subject to any disclaimer, the term of this patent is extended or adjusted under 35 U.S.C. 154(b) by 275 days.

(21) Appl. No.: 16/122,707

(22) Filed: Sep. 5, 2018

(65) Prior Publication Data

US 2019/0072527 A1 Mar. 7, 2019

Related U.S. Application Data

(60) Provisional application No. 62/605,999, filed on Sep. 5, 2017.

(51) Int. Cl.
*G01N 29/265* (2006.01)
*G01N 29/04* (2006.01)
(Continued)

(52) U.S. Cl.
CPC ........... *G01N 29/265* (2013.01); *G01N 29/04* (2013.01); *G01N 29/225* (2013.01);
(Continued)

(58) Field of Classification Search
CPC ....... G01N 2291/048; G01N 2291/102; G01N 2291/02475; G01N 2291/02483;
(Continued)

(56) References Cited

U.S. PATENT DOCUMENTS 4,674,333 A * 6/1987 Jindo ..................... G01H 3/125
73/606
5,319,977 A * 6/1994 Quate ..................... G01H 3/125
310/336
(Continued)

FOREIGN PATENT DOCUMENTS

| JP | 2003215113 A | * | 7/2003 | |
| JP | 2005265996 A | | 9/2005 | |
| WO | WO-2016097390 A1 | * | 6/2016 | ........... A01N 1/0278 |

OTHER PUBLICATIONS

Jain et al, Dielectric and Piezoelectric Properties of PVDF/PZT Composites: A Review, Polymer Engineering and Science—2015 (Year: 2015).*
(Continued)

*Primary Examiner* — David L Singer
(74) *Attorney, Agent, or Firm* — Kunzler Bean & Adamson

(57) ABSTRACT

An apparatus includes an XY scanning mechanism, a first transducer configured to transmit a sound wave, a second transducer configured to receive the sound wave, and a tray configured to hold a material. The tray is coupled to the XY scanning mechanism and located beneath the first transducer and the second transducer is located on a bottom side of the tray below the material. The tray is moved in an XY pattern along an X axis and a Y axis in response to an XY scanning mechanism controller mechanically moving the XY scanning mechanism while the first transducer is positioned in a stationary location along a vertical axis perpendicular to the tray. The first transducer transmits sound waves into the material and the second transmitter receives the transmitted sound waves at each XY position.

20 Claims, 3 Drawing Sheets

(51) Int. Cl.
  *G01N 29/27* (2006.01)
  *G01N 29/24* (2006.01)
  *G01N 29/28* (2006.01)
  *G01N 29/22* (2006.01)
  *A61B 8/00* (2006.01)

(52) U.S. Cl.
  CPC .......... *G01N 29/245* (2013.01); *G01N 29/27* (2013.01); *G01N 29/28* (2013.01); *A61B 8/4483* (2013.01); *G01N 2291/02475* (2013.01); *G01N 2291/048* (2013.01); *G01N 2291/102* (2013.01)

(58) Field of Classification Search
  CPC ...... G01N 29/28; G01N 29/04; G01N 29/225; G01N 29/245; G01N 29/265; G01N 29/27; A61B 8/4483
  See application file for complete search history.

(56) References Cited

U.S. PATENT DOCUMENTS

| | | | |
|---|---|---|---|
| 5,402,681 A | 4/1995 | Nakaso et al. | |
| 5,677,488 A * | 10/1997 | Monahan | F16C 19/30 340/682 |
| 6,981,417 B1 * | 1/2006 | Oravecz | G01N 29/0609 73/612 |
| 2002/0075758 A1 * | 6/2002 | Kushibiki | G01H 5/00 367/8 |
| 2002/0189359 A1 * | 12/2002 | Batzinger | G01N 29/28 73/596 |
| 2004/0200284 A1 * | 10/2004 | Kessier | G01N 29/28 73/603 |
| 2005/0157386 A1 * | 7/2005 | Greenwald | G02B 21/34 359/398 |
| 2008/0295600 A1 * | 12/2008 | Simonet | G01N 29/265 73/602 |
| 2009/0303838 A1 * | 12/2009 | Svet | G10K 11/346 367/157 |
| 2010/0121584 A1 * | 5/2010 | Moreau | G01N 29/348 702/56 |
| 2010/0226555 A1 * | 9/2010 | Sandstrom | G01N 29/225 382/131 |
| 2012/0232803 A1 * | 9/2012 | Viola | G01N 29/028 702/19 |
| 2012/0302884 A1 * | 11/2012 | Sandstrom | G01N 29/0672 600/439 |
| 2013/0269441 A1 * | 10/2013 | Doyle | G01N 29/07 73/598 |
| 2018/0000068 A1 * | 1/2018 | Peralta | A01N 1/0278 |

OTHER PUBLICATIONS

PCT/US18/49621, "Notification of Transmittal of the International Search Report and the Written opinion of the International Searching Authority, or the Declaration", International Searching Authority, dated Nov. 5, 2018, pp. 1-8.

* cited by examiner

COMPACT IMMERSION SCANNING SYSTEM FOR HIGH-FREQUENCY SOUND WAVES

CROSS-REFERENCE TO RELATED APPLICATION

This application claims the benefit of U.S. Provisional Patent Application No. 62/605,999 entitled "HIGH-FREQUENCY ULTRASONIC SCANNING SYSTEM FOR EXCISED BIOLOGICAL TISSUE" and filed Sep. 5, 2017, for Timothy E. Doyle, which is incorporated herein by reference.

FIELD

This disclosure relates generally to ultrasonic instrumentation, and more particularly to a compact immersion scanning system for high-frequency sound waves.

BACKGROUND

Ultrasound is a valuable method for inspecting opaque materials for hidden flaws and defects, such as cracks and pores; for characterizing the physical properties of a material, such as the bulk and shear modulus; and for characterizing the microscopic structure (microstructure) of a material, such as found in particulate, laminate, or fiber-reinforced composites. High-frequency ultrasound (10-100 MHz) is particularly sensitive to microstructural features on the micrometer-size scale. These attributes of ultrasound make it useful not only for the nondestructive testing of manufactured materials, but also for inspecting food and other agricultural products, ensuring the integrity of civil engineering structures, and for diagnostic testing in medicine.

SUMMARY

The subject matter of the present application has been developed in response to the present state of the art, and in particular, in response to the shortcomings of conventional high-frequency sound scanning systems, that have not yet been fully solved by currently available techniques. Accordingly, the subject matter of the present application has been developed to provide a compact immersion scanning system for high-frequency sound waves that overcomes at least some of the above-discussed shortcomings of prior art techniques.

An apparatus, in one embodiment, includes an XY scanning mechanism configured to mechanically move in an XY pattern by an XY scanning mechanism controller, a first transducer configured to transmit a sound wave, a second transducer configured to receive the sound wave, and a tray configured to hold a material. In certain embodiments, the tray is coupled to the XY scanning mechanism and located beneath the first transducer and the second transducer is located on a bottom side of the tray below the material. In further embodiments, the tray is moved in an XY pattern along an X axis and a Y axis in response to an XY scanning mechanism controller mechanically moving the XY scanning mechanism while the first transducer is positioned in a stationary location along a vertical axis perpendicular to the tray. In certain embodiments, the first transducer transmits sound waves into the material at each XY position as the tray moves and the second transmitter receives the transmitted sound waves at each XY position for determining characteristics of the material based on the received sound waves.

A system, in one embodiment, includes a sound wave generator configured to generate high-voltage electrical pulses and a signal analyzer. The system, in certain embodiments, includes an apparatus that includes an XY scanning mechanism configured to mechanically move in an XY pattern by an XY scanning mechanism controller, a first transducer configured to transmit a sound wave generated by converting the high-voltage electrical pulses to ultrasonic pulses, a second transducer communicatively coupled to the signal analyzer and configured to receive the sound wave, and a tray configured to hold a material. In one embodiment, the tray is coupled to the XY scanning mechanism and located beneath the first transducer and the second transducer is located on a bottom side of the tray below the material. In further embodiments, the tray is moved in an XY pattern along an X axis and a Y axis in response to the XY scanning mechanism controller mechanically moving the XY scanning mechanism while the first transducer is positioned in a stationary location along a vertical axis perpendicular to the tray. The first transducer may transmit sound waves into the material in the tray at each XY position as the tray moves and the second transmitter may receive the transmitted sound waves at each XY position. The signal analyzer may determine characteristics of the material based on the received sound waves.

In various embodiments, a method includes submersing a material into a tray filled with a liquid. The tray may be coupled to an XY scanning mechanism configured to mechanically move along an X axis and a Y axis in an XY pattern by an XY scanning mechanism controller. In further embodiments, the method includes immersing a first transducer into the tray above the material at a first XY position. The first transducer may be positioned in a stationary location perpendicular to the tray along a vertical axis. In certain embodiments, the method includes transmitting a sound wave into the material using the first transducer and receiving the transmitted sound wave using a second transducer located on a bottom side of the tray below the material. In one embodiment, the method includes moving the tray to a second XY position along the X axis and the Y axis in response to moving the XY scanning mechanism to the second XY position for transmitting the sound wave into the material at the second location and receiving the transmitted sound wave at the second position.

The described features, structures, advantages, and/or characteristics of the subject matter of the present disclosure may be combined in any suitable manner in one or more embodiments and/or implementations. In the following description, numerous specific details are provided to impart a thorough understanding of embodiments of the subject matter of the present disclosure. One skilled in the relevant art will recognize that the subject matter of the present disclosure may be practiced without one or more of the specific features, details, components, materials, and/or methods of a particular embodiment or implementation. In other instances, additional features and advantages may be recognized in certain embodiments and/or implementations that may not be present in all embodiments or implementations.

Further, in some instances, well-known structures, materials, or operations are not shown or described in detail to avoid obscuring aspects of the subject matter of the present disclosure. The features and advantages of the subject matter of the present disclosure will become more fully apparent from the following description and appended claims, or may be learned by the practice of the subject matter as set forth hereinafter.

BRIEF DESCRIPTION OF THE DRAWINGS

In order that the advantages of the subject matter may be more readily understood, a more particular description of the subject matter briefly described above will be rendered by reference to specific embodiments that are illustrated in the appended drawings. Understanding that these drawings depict only typical embodiments of the subject matter and are not therefore to be considered to be limiting of its scope, the subject matter will be described and explained with additional specificity and detail through the use of the drawings, in which.

DETAILED DESCRIPTION

Figure 1:
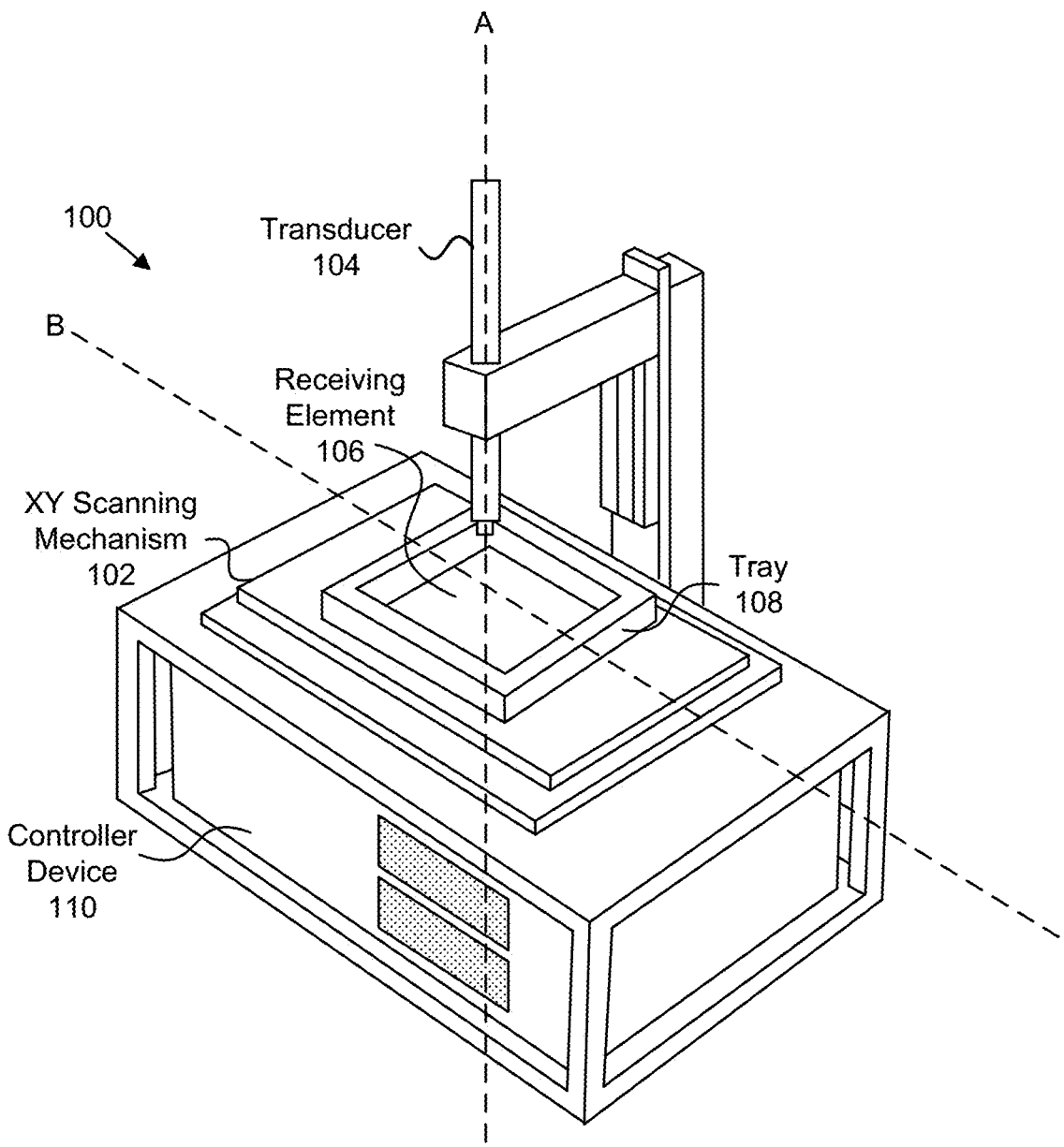
FIG. 1 depicts a perspective view of a system for a compact immersion scanning system for high-frequency sound waves, according to one or more examples of the present disclosure.

Reference throughout this specification to "one embodiment," "an embodiment," or similar language means that a particular feature, structure, or characteristic described in connection with the embodiment is included in at least one embodiment of the present disclosure. Appearances of the phrases "in one embodiment," "in an embodiment," and similar language throughout this specification may, but do not necessarily, all refer to the same embodiment. Similarly, the use of the term "implementation" means an implementation having a particular feature, structure, or characteristic described in connection with one or more embodiments of the present disclosure, however, absent an express correlation to indicate otherwise, an implementation may be associated with one or more embodiments.

An apparatus, in one embodiment, includes an XY scanning mechanism configured to mechanically move in an XY pattern by an XY scanning mechanism controller, a first transducer configured to transmit a sound wave, a second transducer configured to receive the sound wave, and a tray configured to hold a material. In certain embodiments, the tray is coupled to the XY scanning mechanism and located beneath the first transducer and the second transducer is located on a bottom side of the tray below the material. In further embodiments, the tray is moved in an XY pattern along an X axis and a Y axis in response to an XY scanning mechanism controller mechanically moving the XY scanning mechanism while the first transducer is positioned in a stationary location along a vertical axis perpendicular to the tray. In certain embodiments, the first transducer transmits sound waves into the material at each XY position as the tray moves and the second transmitter receives the transmitted sound waves at each XY position for determining characteristics of the material based on the received sound waves.

In one embodiment, the second transducer comprises a film adhered to an interior of a bottom side of the tray. In certain embodiments, the film comprises a piezoelectric polymer film consisting of polyvinylidene difluoride ("PVDF"). In one embodiment, the second transducer is configured to be waterproof.

In some embodiments, the second transducer is integrated into a bottom side of the tray. In further embodiments, the second transducer integrated into the bottom side of the tray comprises a piezoceramic transducer. In various embodiments, the first transducer comprises a narrow-beam transducer.

In one embodiment, the tray is configured to contain an immersion liquid in which the material is submersed. In some embodiments, the first transducer is lowered into the immersion liquid prior to transmitting sound waves through the material. In further embodiments, the material is sealed in a waterproof container prior to submersing the material in the immersion liquid. In one embodiment, the apparatus includes one or more clamps configured to secure the material to the tray while it is submersed in the immersion liquid. The one or more clamps may be operatively coupled to the interior of the bottom side of the tray. In certain embodiments, the waterproof container comprises a second liquid such that the material is acoustically coupled to the waterproof container.

In one embodiment, the XY scanning mechanism is positioned horizontally along the X axis and perpendicular to the first transducer located along the vertical axis. In some embodiments, the received sound waves comprise through-transmission measurements for determining properties of the material, the properties comprising one or more of ultrasonic wave speed, attenuation, spectral properties, and microstructure properties. In further embodiments, the received sound waves comprise pulse-echo measurements for imaging macroscopic structural features of the material, the macroscopic structural features of the material comprising one or more of texture, layering, clustering, defects, cracks, pores, flaws, tumor boundaries, organ boundaries, and vasculature. In some embodiments, the material comprises a biological tissue specimen.

A system, in one embodiment, includes a sound wave generator configured to generate high-voltage electrical pulses and a signal analyzer. The system, in certain embodiments, includes an apparatus that includes an XY scanning mechanism configured to mechanically move in an XY pattern by an XY scanning mechanism controller, a first transducer configured to transmit a sound wave generated by converting the high-voltage electrical pulses to ultrasonic pulses, a second transducer communicatively coupled to the signal analyzer and configured to receive the sound wave, and a tray configured to hold a material. In one embodiment, the tray is coupled to the XY scanning mechanism and located beneath the first transducer and the second transducer is located on a bottom side of the tray below the material. In further embodiments, the tray is moved in an XY pattern along an X axis and a Y axis in response to the XY scanning mechanism controller mechanically moving the XY scanning mechanism while the first transducer is positioned in a stationary location along a vertical axis perpendicular to the tray. The first transducer may transmit sound waves into the material in the tray at each XY position as the tray moves and the second transmitter may receive the transmitted sound waves at each XY position. The signal analyzer may determine characteristics of the material based on the received sound waves.

In one embodiment, the XY scanning mechanism controller is further configured to map a transmitted sound wave to a corresponding scan position of the XY scanning mechanism. In certain embodiments, the sound wave generator, the signal analyzer, and the apparatus are integrated into a single unit.

In various embodiments, a method includes submersing a material into a tray filled with a liquid. The tray may be coupled to an XY scanning mechanism configured to mechanically move along an X axis and a Y axis in an XY pattern by an XY scanning mechanism controller. In further embodiments, the method includes immersing a first transducer into the tray above the material at a first XY position. The first transducer may be positioned in a stationary location perpendicular to the tray along a vertical axis. In certain embodiments, the method includes transmitting a sound wave into the material using the first transducer and receiving the transmitted sound wave using a second transducer located on a bottom side of the tray below the material. In one embodiment, the method includes moving the tray to a second XY position along the X axis and the Y axis in response to moving the XY scanning mechanism to the second XY position for transmitting the sound wave into the material at the second location and receiving the transmitted sound wave at the second position.

FIG. 1 depicts a perspective view of one embodiment of a system 100 for a compact immersion scanning system for high-frequency sound waves. In one embodiment, the system 100 is configured for characterizing and imaging the material properties of small specimens (e.g., 10-100 cm$^2$ in area and 0.2-2.0 cm in thickness) with high-frequency ultrasound (e.g., 10-100 MHz), or other sound waves. The system 100, in certain embodiments, uses through-transmission measurements, pulse-echo measurements, waveform analysis of the signal in the time domain, and/or spectral analysis of the signal in the frequency domain to determine key properties and microscopic features of the specimen including, but not limited to, ultrasonic wave speed, ultrasonic attenuation, and the size of micrometer-scale inclusions.

The system 100, in one embodiment, comprises a mechanical, automated XY scanning system 102; a small diameter (e.g., approximately 1 mm or less) piezoelectric transducer 104 that functions as the transmitting element; an open-top container, dish, or tray 108 to hold liquid (e.g., water or another conductive liquid) in which the material is immersed; a large-area (e.g., 10-100 cm$^2$) piezoelectric transducer/sensor 106 that functions as the receiving element; and a controller device 110 for generating, receiving, and/or processing signals, controlling the XY scanning mechanism 102, and/or the like. The receiving element 106 may be set or mounted at the bottom of the tray 108.

In an example embodiment, during operation of the system 100, the material is fastened on top of the receiving element 106 in the immersion liquid in the tray 108. If the material is sensitive to the immersion liquid, it may be sealed in a leak-proof plastic bag before fastening on top of the receiving element 106. The transmitting element 104 is immersed in the liquid above the material. Either the transmitting element 104 or the tray 108 is moved by the XY scanning mechanism 102 in a two-dimensional pattern to scan the material. Two-dimensional material property images may be constructed of the material by registering the ultrasonic signals with their corresponding scan positions. Applications where the system 100 can be used include, but are not limited to, mapping the pathology of human tissue specimens resected during surgery, biopsy, and other medical procedures; nondestructive evaluation of engine, machine, or electronic components; food inspection procedures; and/or the like.

FIG. 1 depicts the components of the high-frequency ultrasonic scanning system 100, configured to operate with a stationary transmitting transducer 104 and a receiving transducer 106 that moves with the tray 108 in an XY pattern (e.g., left to right and forward to backward) according to the XY scanning mechanism 102.

Figure 3:
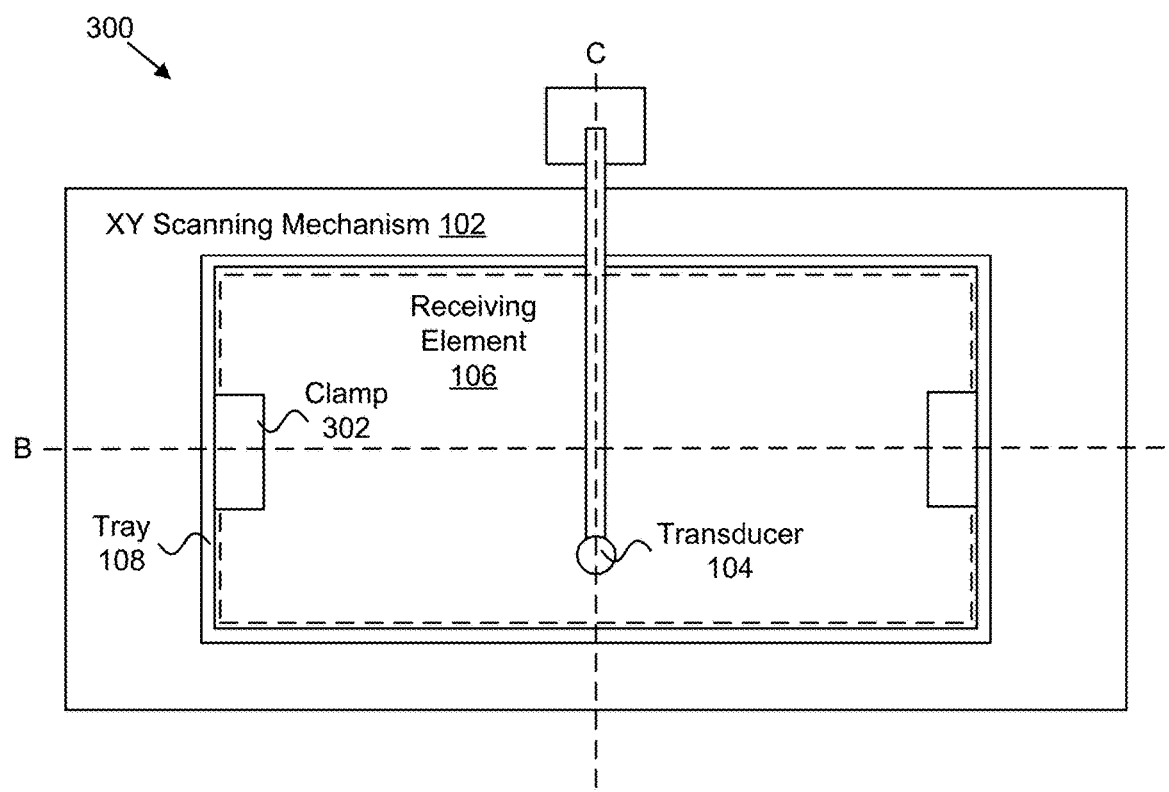
FIG. 3 depicts a top orthographic view of a system for a compact immersion scanning system for high-frequency sound waves, according to one or more examples of the present disclosure.

In the depicted embodiment, as used herein, the XY scanning mechanism 102 provides position control of the tray 108 in two horizontal linear directions (and perpendicular to the transmitting transducer 104), an "X" direction along an axis B (e.g., left to right) and a "Y" direction (e.g., forward to back) along an axis C (depicted in FIG. 3). In certain embodiments, the XY scanning mechanism 102 is assembled using two linear stages, one mounted to the platform of the other such that the axis of motion of the second stage is perpendicular to that of the first, which allows movement in two directions. An example of a two-axis stage is a microscope stage used to position a slide under a lens.

In the depicted embodiment, the tray 108 is mounted, secured, fastened, or the like to the XY scanning mechanism such that the tray 108 is located under the transmitting transducer 104 regardless of the position the XY scanning mechanism 102. In other words, the transmitting transducer 104, when in a stationary position, can be positioned above the tray 108 at every XY position that where the tray 108 can be located so that the transmitting transducer 104 can transmit high-frequency soundwaves through every XY point of a material placed in the tray 108, which can be used to generate a scan of the material or determine other measurements of the material.

In one embodiment, the XY scanning mechanism 102 is controlled using an XY scanning mechanism controller (not shown). The controller may be part of or integrated with the XY scanning mechanism 102. In some embodiments, the controller is located in the controller device 110. The controller, in certain embodiments, is configured to move the XY scanning mechanism 102 in an XY pattern, e.g., left to right along an X axis B until the end of an X row is reached and then move along a Y axis C onto the next Y row and start again at the far left moving along the X axis B until the end of that row is reached, and so on until the material has been fully scanned. In various embodiments, the controller may map a transmitted and received sound wave to a corresponding scan position of the XY scanning mechanism 102.

The transmitting transducer 104, as depicted in FIG. 1, may be fixed in a stationary position along a vertical axis A such that the tray 108 on the XY scanning mechanism 102 moves beneath the transmitting transducer 104. The transmitting transducer 104 may include a pachymeter, an off-the-shelf ultrasonic transducer generally used to measure the thickness of a cornea. The pachymeter may be comprised of a small diameter (e.g., approximately 1 mm) piezoceramic element that generates a narrow-beam high-frequency (e.g., 50 MHz) ultrasound wave pattern. Other examples of transducers that may be used include piezoceramic transducers, for example comprising lead zirconate titanate (PZT) as the ceramic sensing element; piezoelectric polymer transducers, for example comprising polyvinylidene difluoride (PVDF) as the polymer sensing element; capacitive micromachined ultrasonic transducers; ultrasonic transducers based on micro-electro-mechanical systems (MEMS); optical sensors, which measure the sound wave vibrations on the surface of the material using interferometry based measurements; electromagnetic acoustic transducers (EMATs), which use an electromagnetic pulse to generate sound waves in conductive or ferromagnetic materials; and ground motion transducers (geophones) for sensing seismic waves in the earth.

The receiving transducer 106, in one embodiment, is a large-area piezoelectric polymer film consisting of polyvinylidene difluoride ("PVDF"). PVDF film may be configured into large-area sheets that are sensitive to ultrasound across a wide range of frequencies, including 10-100 MHz. To electrically insulate the receiving transducer from the immersion fluid in the tray 108, the PVDF film may be laminated with a waterproof polymer. The receiving transducer 106 may include electric leads, which would also be insulated with a waterproof polymer, for transmitting the received sound waves (and other information including the XY position of the tray or material where the sound waves were received) to a signal analyzer, for example.

In one embodiment, the receiving transducer 106 is permanently mounted on the interior of the bottom side of the tray 108. For instance, the receiving transducer 106 may be adhered, fastened, or the like to the interior of the bottom side of the tray 108. In some embodiments, the receiving transducer 106 is selectively mounted to the interior of the bottom side of the tray 108 using selective mounting means such as hook-and-loop fasteners, magnets, or the like. In one embodiment, the receiving transducer 106 is integrated into the tray 108. For instance, the receiving transducer 106, e.g., a piezoceramic transducer or the PVDF film, may be integrated into the bottom side of the tray 108 when the tray 108 is manufactured. In such an embodiment, the tray 108 is electrically coupled to a signal analyzer or other device for processing the received sound wave signals.

In certain embodiments, the material is secured to the bottom side of the tray 108, and against the receiving transducer 106 using clamps such as spring clamps, friction clamps, and/or the like. The clamps may be secured to the bottom side of the tray 108, to one or more vertical sides of the tray 108, and/or the like. If the material is sensitive to the immersion fluid, the material may be placed into a waterproof container such as a leak-proof, resealable plastic bag. However, in such an embodiment, the material would still need to be acoustically coupled to the inside of the bag, either by its own moisture or by a secondary coupling fluid that the material is not sensitive to.

In one embodiment, when the material is secured onto the receiving transducer 106 in the tray 108, the transmitting transducer 104 is lowered into the immersion fluid and the XY scanning mechanism 102 is positioned such that the transmitting transducer 104 is positioned at a starting point above the material in the tray 108. The material would then be incrementally scanned by transmitting and receiving narrow ultrasonic beam sound waves between the transmitting transducer 104 and the receiving transducer 106 at each XY position of the XY scanning mechanism. Position-dependent ultrasonic signals may be acquired by reading and storing the ultrasonic signal and its corresponding XY position from the receiving transducer 106 at each XY scan position.

In one embodiment, the tray 108 is an open-top container for holding immersion liquid and a material to be scanned. The tray 108 may have various sizes and shape configurations. In one embodiment, the tray 108 is about four inches wide by six inches long by one to two inches deep. In some embodiments, different trays 108 (e.g., trays 108 that are differently sized or shaped) may be interchangeable on the XY scanning mechanism 102 to accommodate different material shapes and sizes. For instance, trays 108 may be selectively coupled to the XY scanning mechanism 102 using a friction fit, snaps, fasteners, magnets, and/or the like.

In one embodiment, the controller device 110 comprises a sound wave generator for controlling the transmitting transducer 104 to generate a sound wave such as a high-frequency ultrasonic signal that goes through the liquid and material in the tray 108 and is received by the receiving transducer 106. As described above, the controller device 110 may include an XY scanning mechanism controller for controlling the position and movement of the XY scanning mechanism 102. The controller device 110 may further comprise a signal analyzer for processing the received sound waves. The signal analyzer may perform various computations and measurements on the received sound waves to determine various characteristics of the material.

For example, the signal analyzer may process the received sound waves to determine through-transmission measurements for determining properties of the material such as ultrasonic wave speed, attenuation, spectral properties, and microstructure properties. In another example, the signal analyzer may process the received sound waves to determine pulse-echo measurements for imaging macroscopic structural features of the material such as texture, layering, clustering, defects, cracks, pores, flaws, tumor boundaries, organ boundaries, and vasculature.

The system 100, in one embodiment, provides greater ease and stability for mounting the material in the tray 108. The material may be mounted on a horizontal surface for scanning the material, which helps to flatten and hold the material in position. This is in contrast to other systems, where the material is mounted and suspended in a vertical orientation on a less stable frame or axis, and then scanned between opposing transducers.

The system 100 is inherently smaller and less complicated than other systems since only one element—either the transmitting element 104 or receiving element 106—requires XY motion for scanning. The large area of the receiving element 106 makes it possible to either keep the receiving element 106 still while moving the transmitting element 104 over the scan area, or to keep the transmitting element 104 still while moving the receiving element 106 over the scan area.

Since the material may be mounted horizontally (flat) and directly against the large-area receiving element, the amount of immersion liquid required can be minimized. This reduces the time for mounting the material and the difficulty of immersing the specimen into a deep tank. For human tissue specimens, for instance, the systm 100 provides a complete mapping of the specimen pathology, in contrast to other through-transmission ultrasound systems that provide analysis for only a few positions on the specimen's margin.

Figure 2:
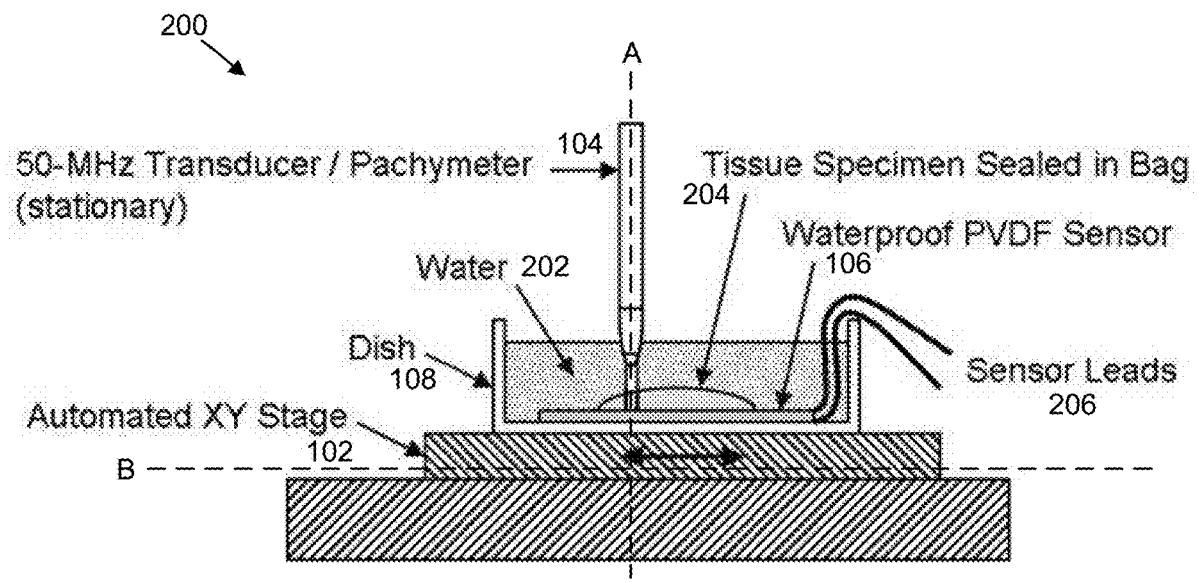
FIG. 2 depicts a side cutaway view of a system for a compact immersion scanning system for high-frequency sound waves, according to one or more examples of the present disclosure.

FIG. 2 illustrates a side perspective view of one embodiment of a compact immersion scanning system 200 for high-frequency sound waves. In one embodiment, the high-frequency ultrasonic scanner system 200 comprises an XY scanning mechanism 102, a transmitting transducer 104 comprising a 50-MHz ultrasonic pachymeter probe fixed in a stationary position along a vertical axis A, and a receiving transducer 106 comprising a large-area PVDF film. An open-top tray 108 may be mounted on top of the XY scanning mechanism 102. The water-proof PVDF sensor 106 is adhered to the bottom of the tray 108, and the tray 108 is filled with water 202 to couple the high-frequency ultrasound to a specimen 204 secured within the tray 108.

Excised tissue specimens 204 are tested by vacuum sealing the specimens 204 in plastic bags, placing each tissue bag in the dish (one at a time), and fastening the tissue bag flat against the PVDF sensor 106 on the bottom of the tray 108 with clamps. The XY scanner mechanism 102 moves in an XY pattern along an X axis B and a Y axis C to scan the specimen beneath the stationary 50-MHz pachymeter 104 immersed in the water 202. Both through-transmission and pulse-echo measurements are acquired and sent to a controlling device 110, or other computing device, using sensor leads 206 to measure the specimen's 204 thickness, ultrasonic wave speed, ultrasonic attenuation, ultrasonic spectra, and/or other characteristics of the specimen 204.

FIG. 3 depicts a top perspective view of a compact immersion scanning system 300 for high-frequency sound waves. In one embodiment, the system 300 includes an XY scanning mechanism 102 that is configured to move in an XY pattern along an X axis B and a Y axis C beneath a stationary transducer 104. A material may be placed in the tray 108 and secured against a receiving transducer 106 using clamps 302.

The XY scanning mechanism 102 may be positioned in a (0,0) position to start the scan, which may correspond to the top left corner. The transmitting transducer 104 may generate a sound wave at that position, which the receiving transducer 106 receives as it travels through the material in the tray 108. The XY scanning mechanism 102 may then be moved to the next XY position (1,0) along the X axis B where another scan is performed, and so on until the entire material is scanned.

The sound wave information and the XY position corresponding to each received sound wave is sent to a computing device such as the controlling device 110 or another computing device where it can be processed, analyzed, and/or the like to generate a graphical scan of the material, to determine various characteristics and properties of the material, and/or the like.

Figure 4:
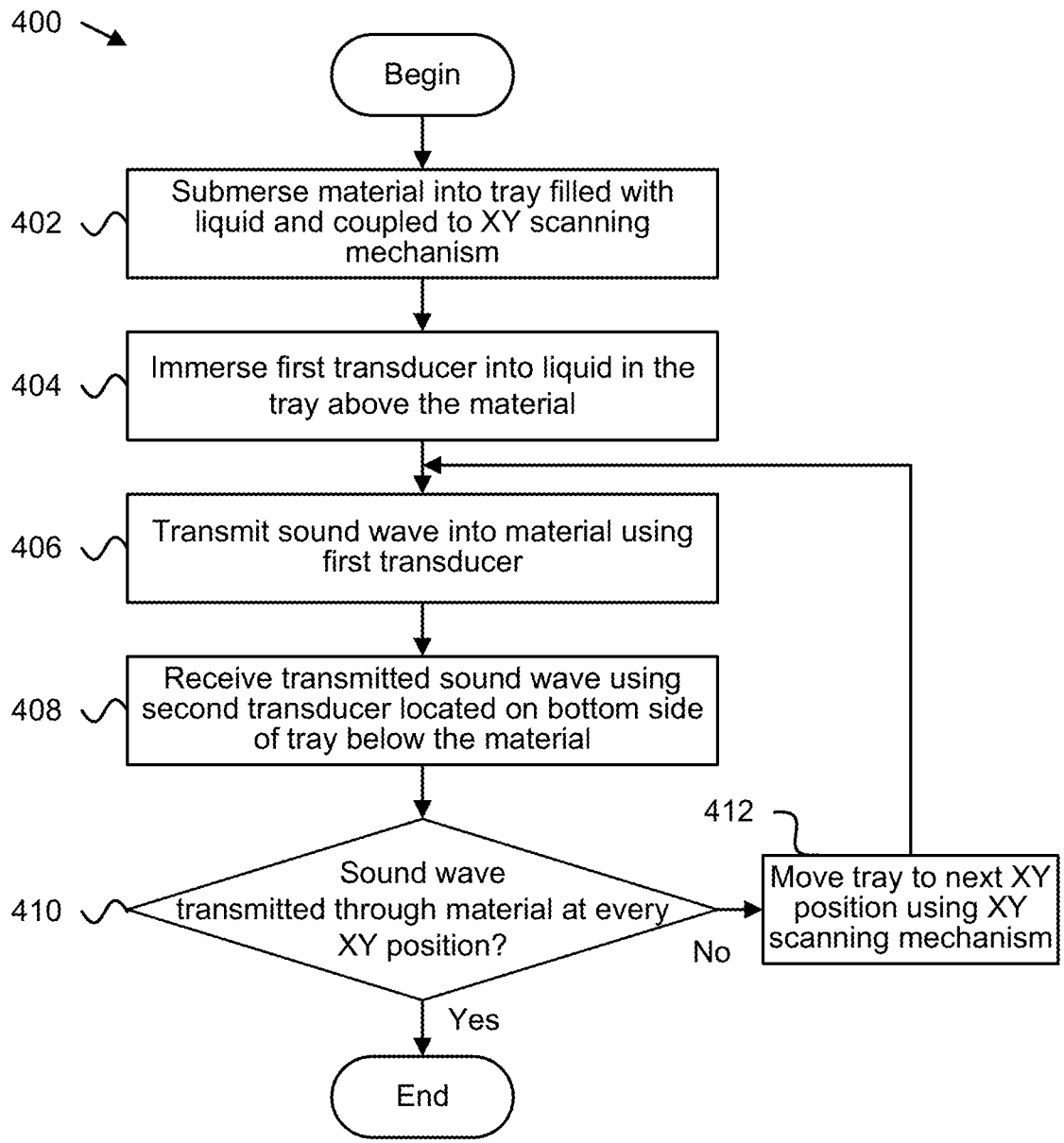
FIG. 4 depicts a schematic flow chart of a method for using a compact immersion scanning system for high-frequency sound waves, according to one or more examples of the present disclosure.

FIG. 4 depicts one embodiment of a method 400 for scanning a material using high-frequency sound waves. In one embodiment, the method 400 begins and submerses 402 a material into a tray 108 filled with a liquid such as water. The tray 108 may be coupled to an XY scanning mechanism 102 configured to mechanically move along an X axis B and a Y axis C in an XY pattern by an XY scanning mechanism controller.

The method 400, in further embodiments, immerses 404 a first transducer 104 into the tray 108 above the material at a first XY position. The first transducer 104 positioned in a stationary location perpendicular to the tray 108 along a vertical axis A. In some embodiments, the method 400 transmits 406 a sound wave into the material using the first transducer 104.

In certain embodiments, the method 400 receives 408 the transmitted sound wave using a second transducer 106 located on a bottom side of the tray 108 below the material. The method 400 determines 410 whether a sound wave has been transmitted through the material at every XY position—in other words, whether the entire material has been scanned. If not, then the method 400 moves 412 the tray 108 to a second XY position along the X axis B and the Y axis C in response to moving the XY scanning mechanism 102 to the second XY position for transmitting the sound wave into the material at the second location and receiving the transmitted sound wave at the second position. Otherwise, the method 400 ends.

In the above description, certain terms may be used such as "up," "down," "upper," "lower," "horizontal," "vertical," "left," "right," "over," "under" and the like. These terms are used, where applicable, to provide some clarity of description when dealing with relative relationships. But, these terms are not intended to imply absolute relationships, positions, and/or orientations. For example, with respect to an object, an "upper" surface can become a "lower" surface simply by turning the object over. Nevertheless, it is still the same object. Further, the terms "including," "comprising," "having," and variations thereof mean "including but not limited to" unless expressly specified otherwise. An enumerated listing of items does not imply that any or all of the items are mutually exclusive and/or mutually inclusive, unless expressly specified otherwise. The terms "a," "an," and "the" also refer to "one or more" unless expressly specified otherwise. Further, the term "plurality" can be defined as "at least two." Moreover, unless otherwise noted, as defined herein a plurality of particular features does not necessarily mean every particular feature of an entire set or class of the particular features.

Additionally, instances in this specification where one element is "coupled" to another element can include direct and indirect coupling. Direct coupling can be defined as one element coupled to and in some contact with another element. Indirect coupling can be defined as coupling between two elements not in direct contact with each other, but having one or more additional elements between the coupled elements. Further, as used herein, securing one element to another element can include direct securing and indirect securing. Additionally, as used herein, "adjacent" does not necessarily denote contact. For example, one element can be adjacent another element without being in contact with that element.

As used herein, the phrase "at least one of", when used with a list of items, means different combinations of one or more of the listed items may be used and only one of the items in the list may be needed. The item may be a particular object, thing, or category. In other words, "at least one of" means any combination of items or number of items may be used from the list, but not all of the items in the list may be required. For example, "at least one of item A, item B, and item C" may mean item A; item A and item B; item B; item A, item B, and item C; or item B and item C. In some cases, "at least one of item A, item B, and item C" may mean, for example, without limitation, two of item A, one of item B, and ten of item C; four of item B and seven of item C; or some other suitable combination.

Unless otherwise indicated, the terms "first," "second," etc. are used herein merely as labels, and are not intended to impose ordinal, positional, or hierarchical requirements on the items to which these terms refer. Moreover, reference to, e.g., a "second" item does not require or preclude the existence of, e.g., a "first" or lower-numbered item, and/or, e.g., a "third" or higher-numbered item.

As used herein, a system, apparatus, structure, article, element, component, or hardware "configured to" perform a specified function is indeed capable of performing the specified function without any alteration, rather than merely having potential to perform the specified function after further modification. In other words, the system, apparatus, structure, article, element, component, or hardware "configured to" perform a specified function is specifically selected, created, implemented, utilized, programmed, and/or designed for the purpose of performing the specified function. As used herein, "configured to" denotes existing characteristics of a system, apparatus, structure, article, element, component, or hardware which enable the system, apparatus, structure, article, element, component, or hardware to perform the specified function without further modification. For purposes of this disclosure, a system, apparatus, structure, article, element, component, or hardware described as being "configured to" perform a particular function may additionally or alternatively be described as being "adapted to" and/or as being "operative to" perform that function.

The schematic flow chart diagrams included herein are generally set forth as logical flow chart diagrams. As such, the depicted order and labeled steps are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

The present subject matter may be embodied in other specific forms without departing from its spirit or essential characteristics. The described embodiments are to be considered in all respects only as illustrative and not restrictive. All changes which come within the meaning and range of equivalency of the claims are to be embraced within their scope.

What is claimed is:

1. An apparatus, comprising:
    an XY scanning mechanism configured to mechanically move in an XY pattern by an XY scanning mechanism controller;
    a first transducer configured to transmit a sound wave;
    a second transducer configured to receive the sound wave; and
    a tray configured to hold a material, the tray coupled to the XY scanning mechanism and located beneath the first transducer, the second transducer located within the tray on a bottom side of the tray directly below the material such that the second transducer moves with the tray as the tray is moved, the XY scanning mechanism configured to accommodate interchangeable trays of various shapes and sizes using a selective fit,
    wherein the tray is moved in an XY pattern along an X axis and a Y axis in response to the XY scanning mechanism controller mechanically moving the XY scanning mechanism while the first transducer is positioned in a stationary location along a vertical axis perpendicular to the tray, the first transducer transmitting sound waves into the material in the tray at each XY position as the tray moves, the second transducer receiving the transmitted sound waves at each XY position for determining characteristics of the material based on the received sound waves.

2. The apparatus of claim 1, wherein the second transducer comprises a film adhered to an interior of a bottom side of the tray.

3. The apparatus of claim 2, wherein the film comprises a piezoelectric polymer film consisting of polyvinylidene difluoride ("PVDF").

4. The apparatus of claim 2, wherein the second transducer is configured to be waterproof.

5. The apparatus of claim 1, wherein the second transducer is integrated into a bottom side of the tray.

6. The apparatus of claim 5, wherein the second transducer integrated into the bottom side of the tray comprises a piezoceramic transducer.

7. The apparatus of claim 1, wherein the first transducer comprises a narrow-beam transducer.

8. The apparatus of claim 1, wherein the tray is configured to contain an immersion liquid in which the material is submersed.

9. The apparatus of claim 8, further comprising means for lowering the first transducer into the immersion liquid prior to transmitting sound waves through the material.

10. The apparatus of claim 8, wherein the material is sealed in a waterproof container prior to submersing the material in the immersion liquid.

11. The apparatus of claim 10, further comprising one or more clamps configured to secure the material to the tray while it is submersed in the immersion liquid, the one or more clamps operatively coupled to the interior of the bottom side of the tray.

12. The apparatus of claim 10, wherein the waterproof container comprises a second liquid such that the material is acoustically coupled to the waterproof container.

13. The apparatus of claim 1, wherein the XY scanning mechanism is positioned horizontally along the X axis and perpendicular to the first transducer located along the vertical axis.

14. The apparatus of claim 1, wherein the received sound waves comprise through-transmission measurements for determining properties of the material, the properties comprising one or more of ultrasonic wave speed, attenuation, spectral properties, and microstructure properties.

15. The apparatus of claim 1, wherein the received sound waves comprise pulse-echo measurements for imaging macroscopic structural features of the material, the macroscopic structural features of the material comprising one or more of texture, layering, clustering, defects, cracks, pores, flaws, tumor boundaries, organ boundaries, and vasculature.

16. The apparatus of claim 1, wherein the material comprises a biological tissue specimen.

17. A system, comprising:
    a sound wave generator configured to generate high voltage electrical pulses;
    a signal analyzer; and
    an apparatus comprising:
        an XY scanning mechanism configured to mechanically move in an XY pattern by an XY scanning mechanism controller;
        a first transducer configured to transmit a sound wave generated by converting the electrical pulses to ultrasonic pulses;
        a second transducer configured to receive the sound wave, the second transducer communicatively coupled to the signal analyzer; and
        a tray configured to hold a material, the tray coupled to the XY scanning mechanism and located beneath the first transducer, the second transducer located within the tray on a bottom side of the tray directly below the material such that the second transducer moves with the tray as the tray is moved, the XY scanning mechanism configured to accommodate interchangeable trays of various shapes and sizes using a selective fit, wherein the tray is moved in an XY pattern along an X axis and a Y axis in response to the XY scanning mechanism controller mechanically moving the XY scanning mechanism while the first transducer is positioned in a stationary location along a vertical axis perpendicular to the tray, the first transducer transmitting sound waves into the material in the tray at each XY position as the tray moves, the second transmitter transducer receiving the transmitted sound waves at each XY position, the signal analyzer determining characteristics of the material based on the received sound waves.

18. The system of claim 17, wherein the XY scanning mechanism controller is further configured to map a transmitted sound wave to a corresponding scan position of the XY scanning mechanism.

19. The system of claim 17, wherein the sound wave generator, the signal analyzer, and the apparatus are integrated into a single unit.

20. A method, comprising:

submersing a material into a tray filled with a liquid, the tray coupled to an XY scanning mechanism configured to mechanically move along an X axis and a Y axis in an XY pattern by an XY scanning mechanism controller, the XY scanning mechanism configured to accommodate interchangeable trays of various shapes and sizes using a selective fit;

immersing a first transducer into the tray above the material at a first XY position, the first transducer positioned in a stationary location perpendicular to the tray along a vertical axis;

transmitting a sound wave into the material using the first transducer;

receiving the transmitted sound wave using a second transducer located within the tray on a bottom side of the tray directly below the material such that the second transducer moves with the tray as the tray is moved; and moving the tray to a second XY position along the X axis and the Y axis in response to moving the XY scanning mechanism to the second XY position for transmitting the sound wave into the material at the second location and receiving the transmitted sound wave at the second position.

\* \* \* \* \*